(12) United States Patent
Roberts et al.

(10) Patent No.: US 7,704,278 B2
(45) Date of Patent: Apr. 27, 2010

(54) METHOD AND APPARATUS FOR ENHANCED CORNEAL ACCOMMODATION

(75) Inventors: Cynthia J. Roberts, Columbus, OH (US); Edwin J. Sarver, Carbondale, IL (US); James R. Marous, South Vienna, OH (US)

(73) Assignee: CRS & Associates, Columbus, OH (US)

( * ) Notice: Subject to any disclaimer, the term of this patent is extended or adjusted under 35 U.S.C. 154(b) by 1077 days.

(21) Appl. No.: 10/572,084

(22) PCT Filed: Oct. 6, 2004

(86) PCT No.: PCT/US2004/032897

§ 371 (c)(1),
(2), (4) Date: Mar. 16, 2006

(87) PCT Pub. No.: WO2005/034730

PCT Pub. Date: Apr. 21, 2005

(65) Prior Publication Data

US 2007/0106376 A1    May 10, 2007

Related U.S. Application Data

(60) Provisional application No. 60/508,924, filed on Oct. 6, 2003.

(51) Int. Cl.
*A61F 2/14*    (2006.01)
*A61F 9/007*   (2006.01)

(52) U.S. Cl. .......................................... 623/4.1; 606/5

(58) Field of Classification Search ......... 623/4.1–5.12; 606/5
See application file for complete search history.

(56) References Cited

U.S. PATENT DOCUMENTS

| 6,258,082 | B1 | 7/2001 | Lin | |
|---|---|---|---|---|
| 6,969,386 | B2 * | 11/2005 | Tamayo et al. | 606/5 |
| 7,273,277 | B2 * | 9/2007 | Sarver | 351/200 |
| 7,582,081 | B2 * | 9/2009 | Hofer et al. | 606/5 |
| 2003/0176855 | A1 * | 9/2003 | Gross et al. | 606/5 |
| 2006/0015090 | A1 * | 1/2006 | Roberts et al. | 606/5 |

* cited by examiner

*Primary Examiner*—Suzette J Gherbi
(74) *Attorney, Agent, or Firm*—William Greener; Bond, Schoeneck & King, PLLC (57) ABSTRACT

A method and apparatus related to enhancing corneal accommodation to address the effect of presbyopia. Corneal/scleral topology measurements in accommodating and non-accommodating states are indicative of a presbyopic subject's nominal corneal accommodative power. A desired accommodative power intended to improve on the effect of presbyopia can be determined, suggesting a selective biomechanical intervention in the corneal structure outside of the optical zone to create flexure regions. These flexure regions would allow enhanced corneal accommodation upon presentation of an accommodating stimulus. Intervention could be in the form of, for example, corneal surface ablation, intrastromal ablation, conductive keratoplasty (CK), laser thermal keratoplasty (LTK), and corneal and/or scleral implants. An improved topology measuring apparatus having an improved field of view and other attributes is disclosed.

3 Claims, 9 Drawing Sheets

METHOD AND APPARATUS FOR ENHANCED CORNEAL ACCOMMODATION

CROSS-REFERENCE TO RELATED APPLICATIONS

The present application is the U.S. National Stage filing under 35 U.S.C. § 371 of International Application No. PCT/US04/032897 filed Oct. 6, 2004 and published on Apr. 21, 2005 as Publication No. WO 2005/034730, which claims priority to U.S. Provisional Application No. 60/508,924 filed Oct. 6, 2003.

BACKGROUND OF THE INVENTION

1. Field of the Invention

Embodiments of the invention include methods and apparatus that are generally directed to addressing the effect of presbyopia, and which are more particularly directed to addressing solutions to the problem of presbyopia through corneal accommodation.

2. Description of Related Art

Figure 1:
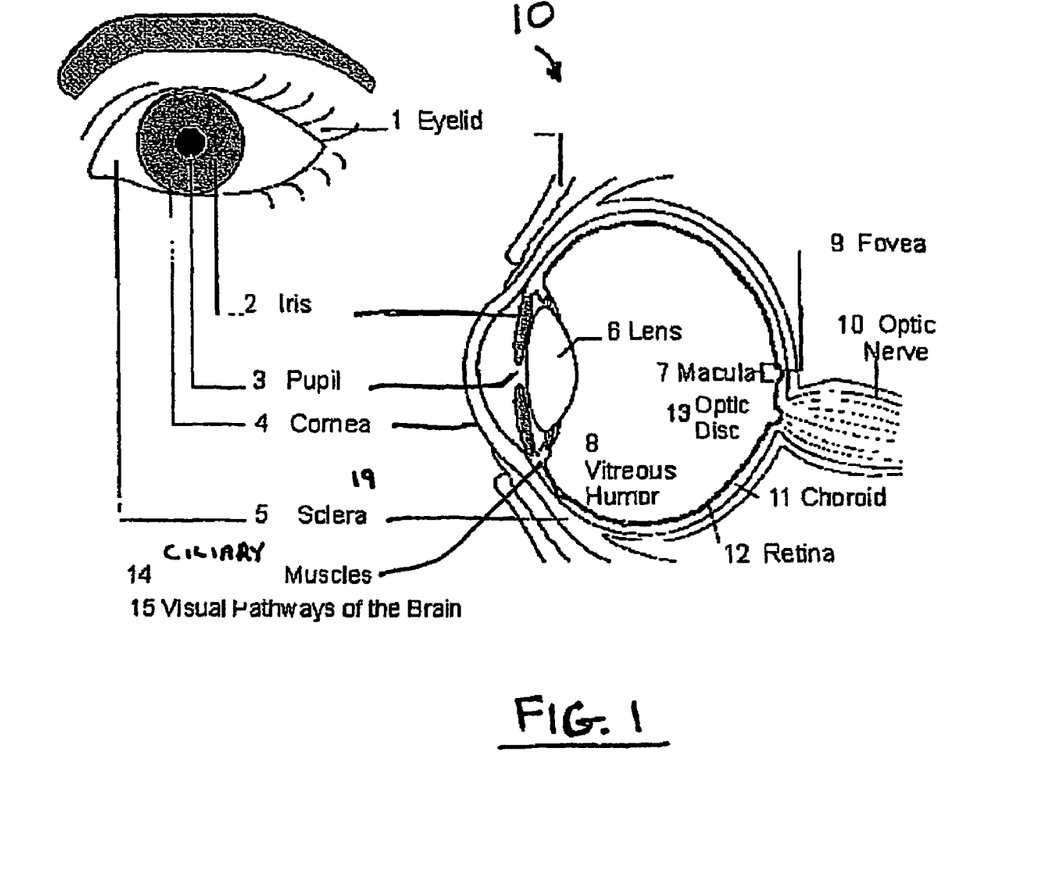
FIG. 1 is a diagrammatic illustration of human eye anatomy in cross-section showing the structural components of the eye.

The eye is a multi-component structure providing multiple functions for forming images and enabling sight. A master diagram of the basic anatomy of the human eye 10 is shown in FIG. 1. In very general terms, the anterior portion 19 of the eye includes the cornea 4 and the sclera 5. The cornea is the outer, transparent, domelike structure that covers the iris 2, pupil 3, and anterior chamber. The cornea provides approximately seventy percent of the optical power of the eye. The tough, white, outer layer of the eyeball is called the sclera. In combination with the cornea, the sclera protects the entire eyeball. The crystalline lens 6 is located posterior to the cornea and is held in place by fibers controlled by the ciliary muscles, which enable the crystalline lens to change shape for focusing. The retina 12, located at the back of the eye, is the image forming surface of the eye.

The total eye structure operates to receive light coming from an object and form an image of the object on the retina. As mentioned above, the cornea provides the bulk (~70%) of the refractive power of the eye for focusing incoming light onto the retina Common vision defects referred to as near-sightedness (myopia) and farsightedness (hyperopia) typically result from a misshaped corneal surface that either provides too much focusing power or too little focusing power resulting, in any event, in a blurry image. The crystalline lens and the muscle (ciliary) control structures associated therewith provide the eyes with the ability to accommodate; that is, to focus both on objects that are very far away and objects that are very close. However, with age, the crystalline lens in the human eye stiffens and loses its ability to change its shape and/or position in response to the desire to view an object that is close to the viewer's eyes. This condition is referred to as presbyopia, which is the inability of the eye to accommodate. Unfortunately, one hundred percent of the population will develop presbyopia by the time they are fifty years old, give or take several years.

Presbyopia is typically addressed by auxiliary lenses in the form of spectacles or contact lenses that provide the extra focusing power for viewing close-up objects. Spectacle lenses can be of the bifocal or multi-focal type, which provide different lens regions with different focusing powers so that a range of near distance viewing is made possible. Alternatively, contact lenses of the alternating vision type or the simultaneous vision type provide either multiple viewing zones similar to multi-focal spectacles, or provide a near focus and a far focus image simultaneously and rely on the brain to discriminate for the actual view.

Due to the enormous market for presbyopia correction, new methods and devices for addressing the problem are in constant development. For example, scleral bands, refractive laser surgery, accommodating intraocular lenses (IOLs) and other techniques are being used to treat presbyopia. However, treatments to date have not provided optimized results, and many of the proposed treatments are severely invasive in nature and thus traumatize the optical zone of the eye.

Accordingly, the inventor has recognized the need for a method and apparatus improvement useful for addressing the problem of presbyopia, and that overcome the shortcomings in the current state of the art, and which offer benefits and advantages associated with the successful treatment of presbyopia.

SUMMARY OF THE INVENTION

An embodiment of the invention is directed to a method for enhancing corneal accommodation to address the effect of presbyopia. The method includes the steps of making a predetermined biomechanical alteration in a subject's corneal structure to create one or more inflection regions in the cornea. The inflection region(s) would provide enhanced flexure of the cornea upon exposure to an accommodative or near field stimulus resulting in increased corneal (corneal/scleral) curvature upon contraction of the ciliary muscle structure. An aspect of this embodiment involves making a topologic measurement over a corneal and scleral region of the subject's cornea in an accommodative or near field state, making another topologic measurement over the corneal and scleral region of the subject's cornea and sclera in a non-accommodative or optical far field state, and determining the difference between the measured topologic data in the two accommodative states. Once the subject's corneal accommodative capability is determined, the difference between that and an enhanced accommodative capability sufficient to address some, or all, of the subject's presbyopia can be used to further determine how much additional corneal movement would be required to provide the correction. A skilled practitioner can then employ empirical, predictive and analytic techniques to biomechanically alter the corneal structure outside of the optical zone to create inflection regions as referred to above. In an aspect of the embodiment, the method is not limited to obtaining topological information in only two accommodative states, but may include any number of selected accommodative distances. The accommodative states can be induced discreetly and will involve static measurements of the topologic parameters of interest. Alternatively, the accommodative states can be induced continuously over a variation of distances, involving dynamic measurement. Furthermore, it would not be necessary to make the accommodative topology measurements in any particular order or within a particular timeframe. The skilled practitioner can best determine these considerations. The various accommodative states at which measurement data is to be obtained can be induced in ways well known to those skilled in the art, including, but not limited to, optical and pharmacological techniques. Various forms of application of the biomechanical alteration of the subject's cornea are available. For example, the location, extent, and depth of a corneal surface ablation may be used to create suitable inflection regions in the corneal structure to permit and/or increase corneal accommodative power according to the invention. Likewise, appropriate ablation parameters may be determined from the topologic measurement for an intrastromal ablation. Alternative techniques that may be used to create the appropriate biomechanical alteration of the subject's corneal structure include, but are not limited to, conductive keratoplasty (CK), laser thermal keratoplasty (LTK), and corneal and/or scleral implants. In various aspects, corneal/scleral implants may be of a standalone (static) nature or dynamic; i.e., providing a conductive connection to the ciliary muscles or other ocular structure. Because the biomechanical alterations are made in the corneal/scleral structure outside of the optical zone, the methods according to embodiments of the invention as set forth herein are minimally invasive as compared to laser refractive surgical techniques to correct or improve upon the effect of presbyopia.

In accordance with aspects of the methods described herein, the topologic measurements include anterior corneal surface curvature measurements (topography, K-values, profiles, keratometry, etc.) and, elevation data of the corneal/scleral region in the different accommodative states. In an aspect of the embodiment, the corneal curvature and/or elevation data are obtained over regions of the cornea/sclera extending out to, and beyond, about a 7.5 mm horizontal radius from the pupil center or other central ocular reference point.

In another embodiment according to the invention, an improved stereorasterography-based topography measuring apparatus is provided with an increased field of view (FOV) to measure over a desired corneal/scleral region.

DETAILED DESCRIPTION OF A PREFERRED EMBODIMENT OF THE INVENTION

There are numerous reports in the literature of measured changes in the corneal curvature of a subject's eye when an accommodative stimulus is presented to the subject for viewing. The interested reader is referred to Yasuda et al., *Changes in corneal curvature in accommodation, J Cataract Refract Surg* (2003); 29:1297-1301 and He et al., *Change in corneal shape and corneal wave-front aberrations with accommodation, Journal of Vision* (2003); 3: 456-463. This knowledge forms the basis for a method and apparatus according to embodiments of the instant invention for addressing the problem of presbyopia via enhanced corneal accommodation. Through selective or predictive biomechanical intervention in the corneal structure, the range of corneal accommodative power can likely be enhanced such that the presbyopic condition can be improved upon or corrected via compensatory/enhanced corneal accommodation. Results reported by He et al., id., advantageously indicate no direct correlation between corneal accommodation and an increase in ocular aberrations, thus overall vision quality is not expected to suffer due to enhanced accommodative changes in corneal/scleral curvature.

According to an embodiment of the invention, curvature, shape, elevation, and other topologic/topographic measurements are made over a selected corneal/scleral region of a subject's cornea. In an aspect of the embodiment, the selected measurements are made over a scleral region extending out to, or beyond, a horizontal distance of approximately 7.5 mm from a central corneal reference point. One measurement can be obtained with the eye in a non-accommodative state and another measurement can be obtained over the same region with the eye in at least one selected-distance accommodative state. This data can be used to determine the presbyopic subject's nominal corneal accommodative power. From this information, an amount of a desired, enhanced corneal accommodating power can be determined, and a corresponding corneal/scleral radius of curvature and shape factor can be calculated. Consequently, the parameters of a biomechanical intervention in the corneal structure outside of the optical zone of the cornea can be determined and used to create inflection regions in the corneal structure that would enhance the corneal accommodative changes in the eye to provide for accommodation.

Figure 2:
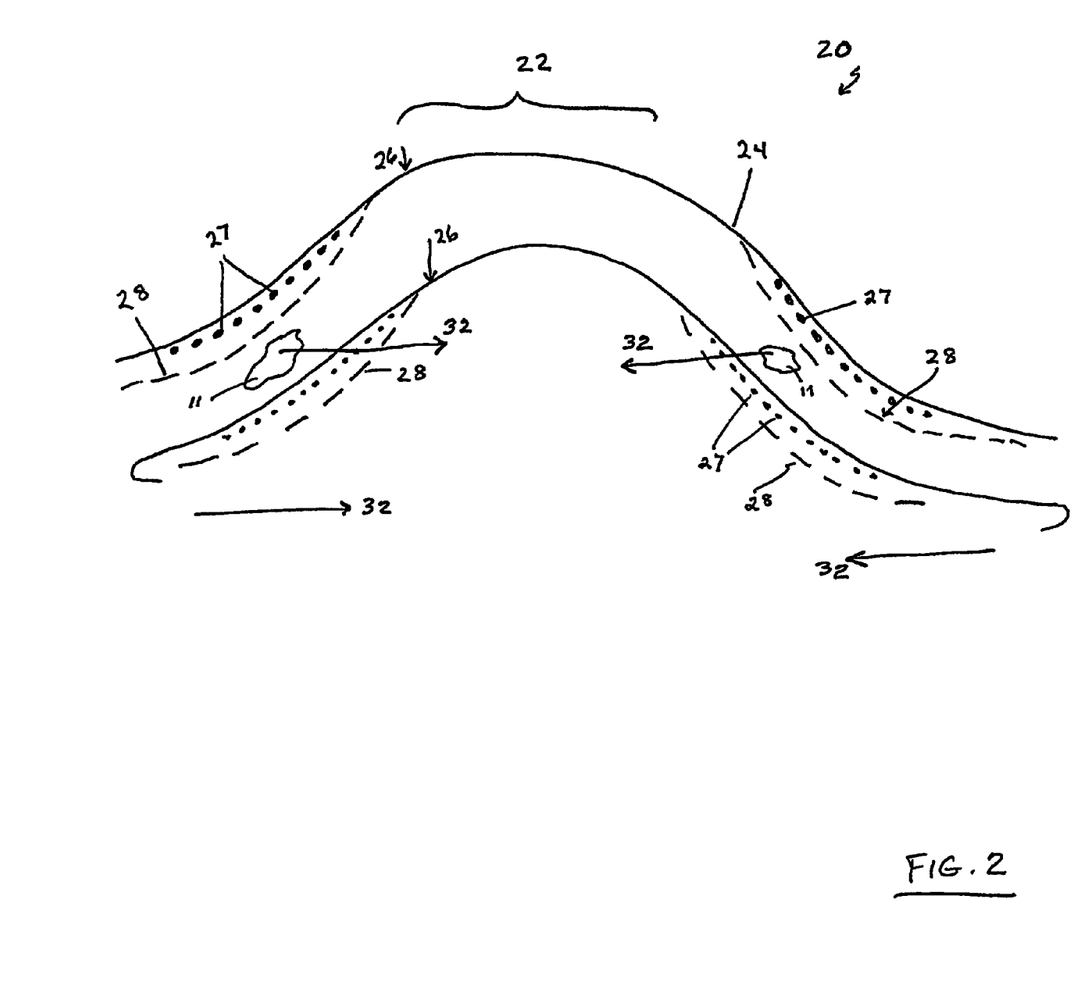
FIG. 2 is an illustrative line drawing of a corneal profile in cross-section showing nominal and enhanced corneal accommodative capability in accordance with an embodiment of the invention.

FIG. 2 schematically illustrates the principal of enhanced corneal accommodation according to an embodiment of the invention. A cross section of cornea 20 includes a central corneal region 22 and a peripheral corneal region 24 outside of the optical zone. The solid lines 26 represent the cross sectional corneal profile in a non-accommodative state. The curves represented by dotted lines 27 represent a nominal corneal accommodative change due to ciliary muscle contraction indicated by arrows 32 in response to an accommodative stimulus, prior to any biomechanical intervention. In combination with the movement of a healthy crystalline lens (not shown), the total accommodative power of the subject's eye is sufficient to create a focused image on the retina of an object at close viewing distance. However, in a presbyopic subject in which the crystalline lens has lost some or all of its accommodative capability (or the lens has been removed), the corneal accommodation represented by dotted line profiles 27 is not sufficient to focus an image of the object at the same up-close distance. According to an embodiment of the invention, the accommodative power of a presbyopic subject, that is to say the corneal accommodative power of a presbyope, can be determined by making measurements of corneal curvature and/or corneal shape and/or corneal elevation in a selected accommodative state and a non-accommodative state. These measurements are then used to determine a desired amount of enhanced corneal accommodative power that would allow the subject to focus an image of the object in the selected accommodative state. The nature and extent of a subject's nominal corneal accommodative power may suggest that the selected topology measurements of the cornea be obtained over a region of the cornea that extends past the central corneal boundary (i.e., the limbus) and into the scleral region. As the eye boundary is limited in the vertical direction by the upper and lower eyelids, conditions may suggest that cornea/scleral curvature and/or shape and/or elevation measurements be obtained over a region extending horizontally out to, or beyond, a radius of approximately 7.5 mm from a central ocular reference point, for example the pupil center. It is to be appreciated that the various accommodative states in which measurement data is obtained can be discreet states at selected accommodation distances. On the other hand, dynamic measurement information could be obtained with a controllable, variable distance target, for example.

Referring again to FIG. 2, according to an embodiment of the invention, the parameters of a biomechanical alteration to the corneal structure outside of the optical zone of the cornea can be empirically determined from the accommodative state measurements. The appropriate biomechanical intervention in the corneal structure would create one or more inflection regions, or regions of enhanced flexibility of the cornea, such that contraction of the ciliary muscle structure represented by the arrows 32 would draw the cornea and/or sclera inward to produce an enhanced corneal accommodation represented by the dashed lines 28. The resulting increased or enhanced corneal accommodative curvature could partially or completely compensate for the presbyopic condition to provide focused imaging of the up-close object.

Figure 7:
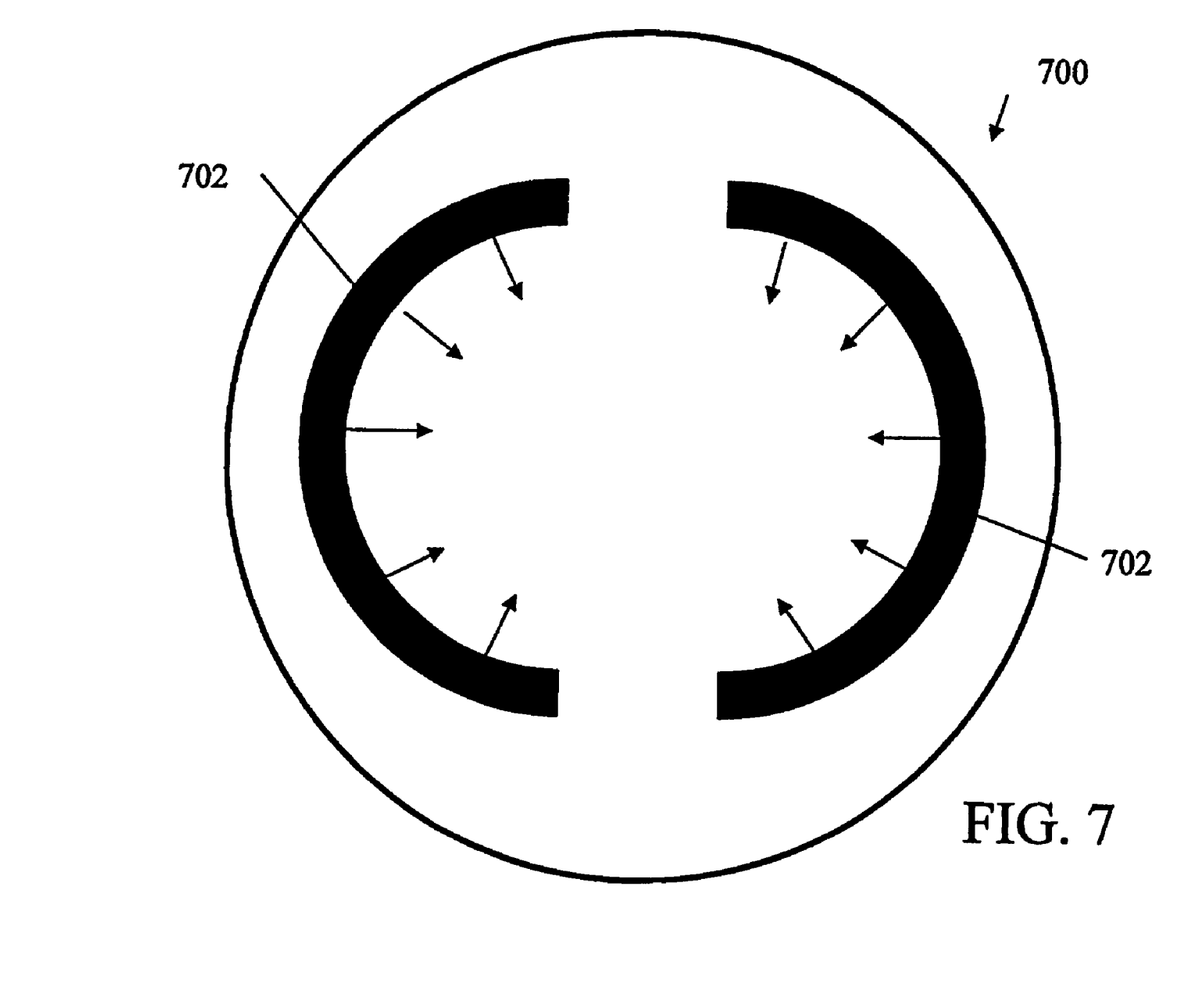
FIG. 7 is a schematic diagram illustrating a corneal implant according to an embodiment of the invention.

According to various aspects of the embodiment, different forms of a suitable biomechanical alteration of the corneal structure may be implemented. For example, corneal surface ablation, intrastromal ablation, conductive keratoplasty (CK), laser thermal keratoplasty (LTK), or incisional techniques such as arcuate keratotomy (AK) or radial keratotomy (RK) are exemplary mechanisms that may be used to achieve the desired biomechanical alteration. An additional, alternative aspect is directed to a static corneal implant; another alternative aspect is directed to a dynamic corneal implant. For example, a silicone, other polymer, hydrogel, or other suitable material implant structure could be coupled to the cornea. The implant would have structural parameters (size, shape, orientation, material combinations) that enhance corneal/scleral curvature in the presence of an accommodative stimulus. This may be realized, for example, by a suitable biomaterial having a shape, thickness, index, size or other parameters that change in response to an accommodative stimulus. The coupling of the implant structure to the corneal structure may be free-standing (static). Alternatively, a dynamic coupling may be realized via electrical and/or optical or other conductive means with the ciliary structure. Although this aspect is referred to herein as a corneal implant, the location of an appropriate structure could include the corneal/scleral surface or any medically appropriate intracorneal/scleral depth. An exemplary corneal implant 700 according to an embodiment of the invention is illustrated in FIG. 7.

The dark arcs 702 illustrate the implant inside the cornea. The arrows represent the motion necessary to produce corneal accommodation.

In effect, any method or technique that will enhance the flexibility and thus the moveability of the corneal/scleral structure in response to an accommodative stimulus and ciliary muscle contraction may be suitable. In particular, application of the biomechanical alteration outside of an optical zone region of the cornea provides a minimally invasive means for enhancing corneal accommodation.

Figure 3:
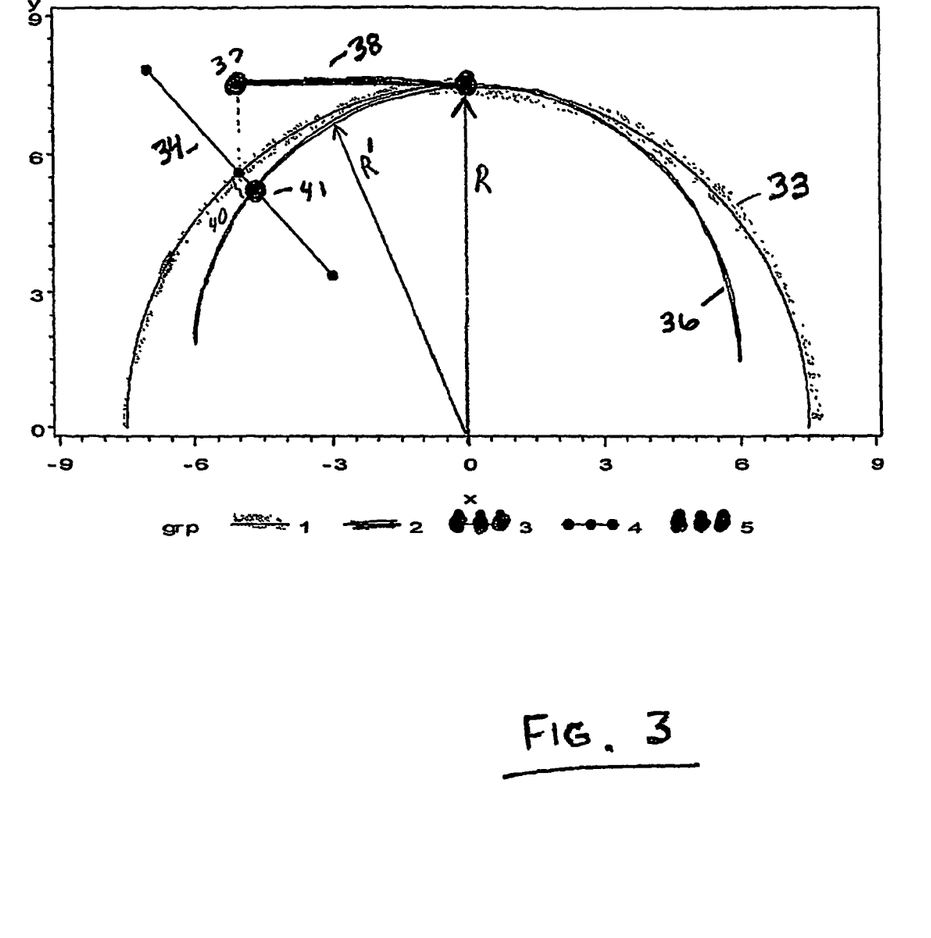
FIG. 3 is a graphical illustration of an exemplary theoretical calculation of enhanced corneal accommodation according to an embodiment of the invention.

An exemplary calculation for enhanced corneal accommodation according to an embodiment of the invention is presented with reference to FIG. 3. In FIG. 3, curve 33 represents the measured profile of a non-accommodating cornea, having a central radius of curvature, R, equal to 7.5 mm, and eccentricity, q, equal to 0.5 (centrally 45 diopters, with decreasing values toward the periphery). In the example, it is desirable to provide an enhanced corneal accommodation of 3 diopters. To achieve this value of enhanced corneal accommodation, the cornea must move inward along the normal to curve 33 as illustrated by line 34 by approximately 44 microns (at reference numeral 40) to maintain an elliptical surface eccentricity value of 0.5, and would have a central radius of curvature, R' equal to 7.0 mm (48 diopters) at a radius of 3 mm from the center (6 mm diameter), as illustrated by curve 36. The left endpoint 37 of line 38 represents the point of the region of interest on the cornea where an inflection region would be created by a biodynamic alteration of the corneal structure to provide the computed change in corneal shape. As such, an inflection region would be created in a region indicated at reference 41.

In an alternative calculation, in order to provide an eccentricity value of 0.8 for the accommodating surface 36 with the same 3 diopters of corneal accommodation, the inward corneal movement would be approximately 32 microns, and an appropriate biomechanical intervention could be empirically determined to provide the necessary degree of enhanced corneal flexure.

A second theoretical calculation is provided for the same non-accommodating surface parameters as in the example above, but accounting for 5 diopters of enhanced corneal accommodation resulting in an accommodating corneal radius of curvature R' equal to 6.75 mm (50 D). To maintain an eccentricity of 0.5, approximately 68 microns of corneal movement would be required. Similarly, to achieve a corneal eccentricity of 0.8, approximately 55 microns of movement would be required.

Based upon the calculations, the nature, location, and extent of a biomechanical alteration of the corneal structure may be determined empirically and thereafter refined, for example, in a manner similarly applied in the development of laser ablation algorithms for refractive surgery procedures.

In an exemplary aspect of the invention, corneal and scleral topology measurements data are obtained over a region of the cornea extending horizontally out to about 7.5 mm from a central origin such as the pupil center. The vertical dimension for measurement will be less, 5-6 mm, as the upper and lower eyelids create hard boundaries. Alternatively, a mechanical means can be used to hold either or both of the eyelids back to increase the vertical extent of measurements.

Figure 4A:
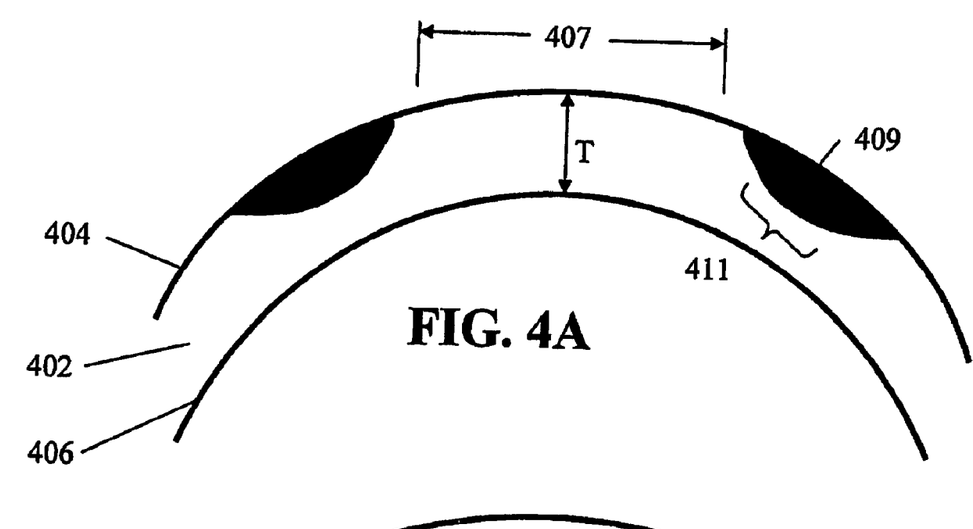
FIGS. 4A and 4B are schematic cross sectional views of a cornea showing a therapeutic tissue alteration according to an embodiment of the invention.
Figure 4B:
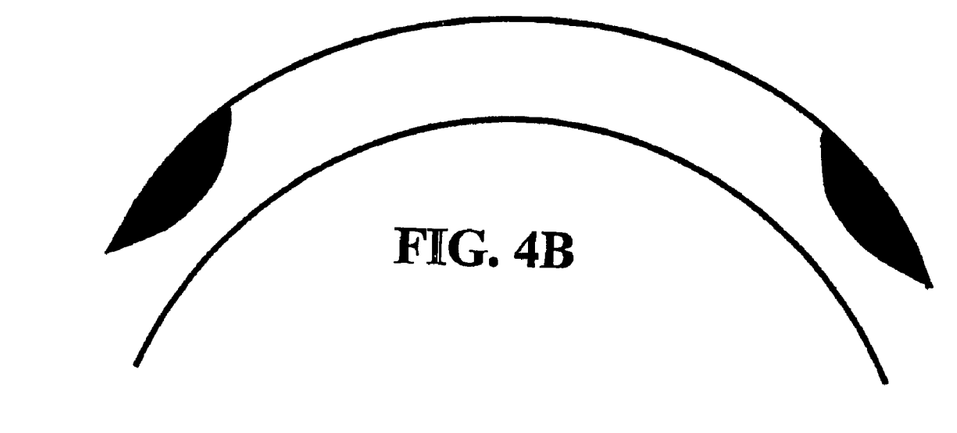

FIGS. 4A and 4B are exemplary illustrations of a method for enhancing corneal accommodation by corneal surface ablation using an excimer laser. In FIG. 4A, cornea 402 is shown in cross section as anterior corneal surface 404 and posterior corneal surface 406. An optical zone region is denoted by 407. Central corneal thickness, T, is on the order of 500 to 550 µm. Dark regions 409 represent regions of corneal surface ablation made by an excimer laser. The laser hardware and software, and utilization of such for ablating human corneas, is well known. Depending upon the accommodative enhancement required for a particular subject, the ablation volume 409 can be adjusted. Subjective feedback may be given in real time, or wavefront or other diagnostic measurements may be obtained dynamically or at predetermined time intervals, to evaluate the efficacy of the treatment. As in conventional refractive laser surgery, a typical residual stromal thickness on the order of 250 µm may limit the ablation depth. The ablated volume shown at 409 will create inflection regions denoted by 411 where the cornea can more easily flex when stimulated by the ciliary muscles or other stimulus. As shown, the surface ablation region 409 is outside of the optical zone 407 of the eye. Although shown as two spots, the ablation pattern will be akin to an annulus around a reference center on the eye. FIG. 4B shows a variation in the placement of the surface ablation relative to FIG. 4A.

Figures 5A, 5B, 5C:
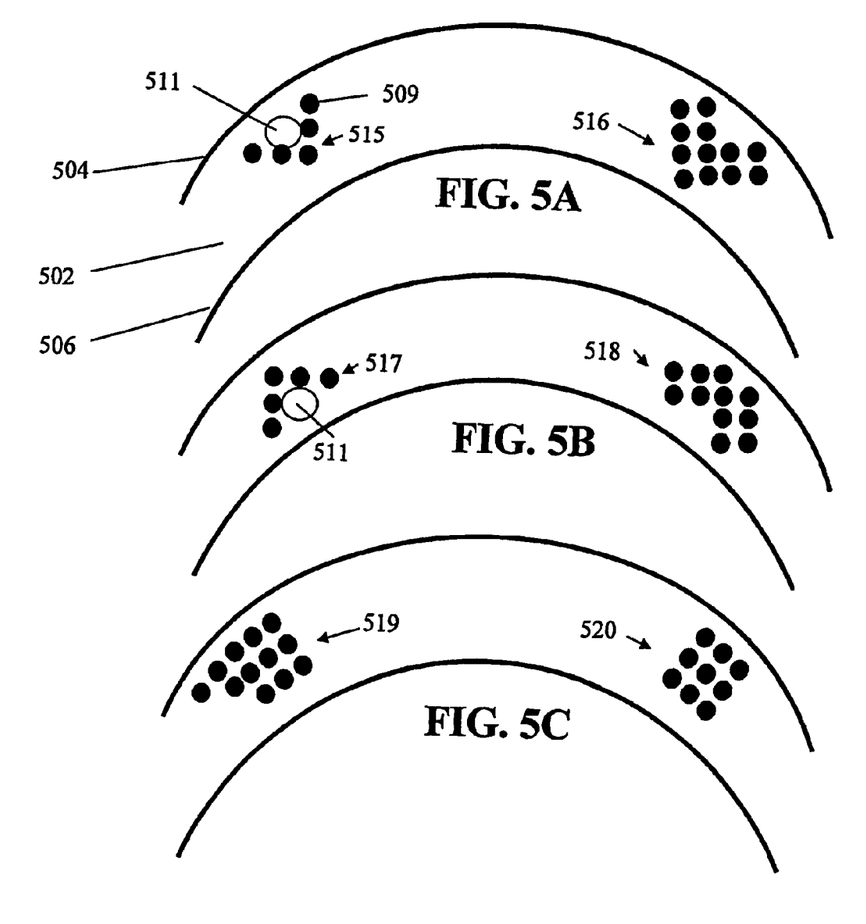
FIGS. 5A, 5B and 5C are schematic cross sectional views of a cornea showing a therapeutic tissue alteration according to an embodiment of the invention.

An exemplary illustration of an alternative technique for enhancing corneal accommodation is shown in FIGS. 5A, 5B and 5C. A cornea 402 is illustrated in cross section as in FIG. 4. In this aspect, inflection regions 511 are created by intrastromal tissue disruption achieved, for example, by femtosecond laser pulses shown as dark circles 509. The dark circles 509 are actually discreet holes within the stroma that, depending on their placement and pattern, create a weakened region where enhanced flexure of the cornea can result from an accommodative stimulus. Various exemplary patterns 515-520 of intrastromal tissue disruption are illustrated. However, it is envisioned that only one of these patterns or a variation thereof as best determined by the surgeon would be used on any given subject. As in the surface ablation example above, treatment may most effectively be determined empirically, at least initially, until a database of historical outcomes can be established. Subjective feedback may be provided by the patient in real time or otherwise, and/or other well known diagnostic means can be employed to determine treatment efficacy. Other intrastromal laser ablation parameters are contemplated, e.g., intrastromal IR laser radiation.

Figure 6A:
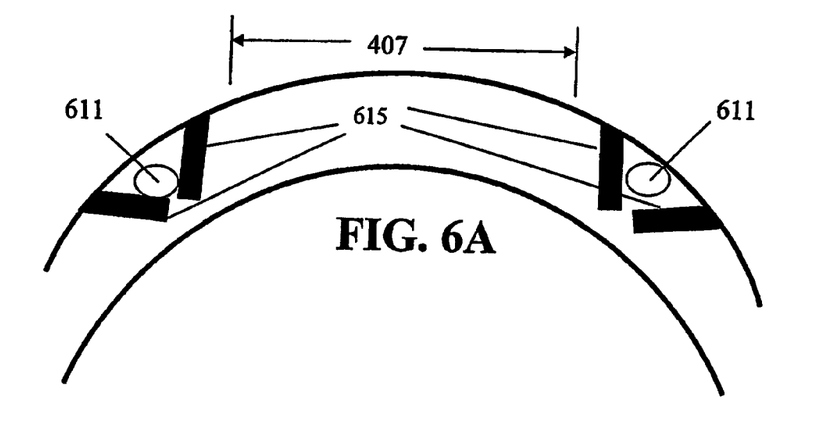
FIGS. 6A and 6B are schematic cross sectional views of a cornea showing a therapeutic tissue alteration according to an embodiment of the invention.
Figure 6B:
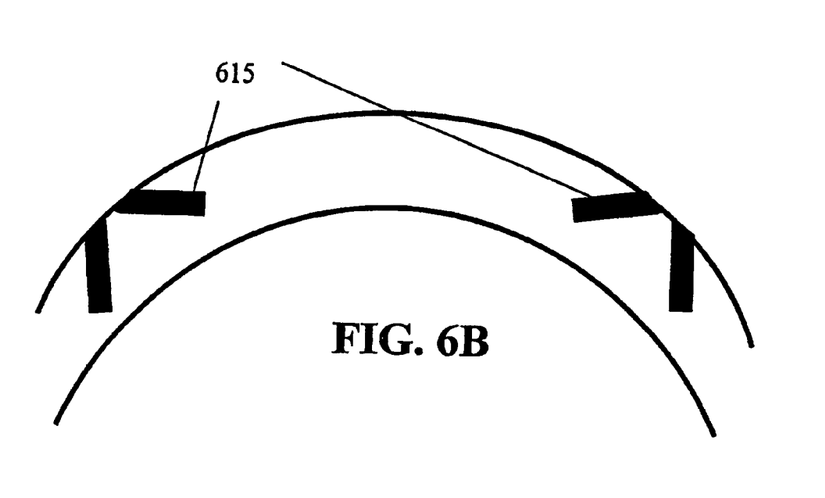

A third exemplary illustration of a corneal enhancement technique embodied by the invention is shown in FIGS. 6A and 6B. Corneal structure is similar to that shown in FIGS. 4 and 5. In FIG. 6, however, inflection regions are created by conductive keratoplasty (CK). The darkened rectangles denoted at 615 are intended to represent cylindrical regions of collagen shrinkage where a CK probe has been inserted into the cornea. Conventional CK is typically performed with probe insertion normal to the corneal surface. As shown in FIG. 6, non-normal insertion is used to effect the different patterns illustrated in FIGS. 6A and 6B. Once again, particular treatment parameters will be determined by the surgeon.

In each of the exemplary illustrations presented immediately above, it will be recognized that corneal tissue modifications may vary in shape, size, depth, contour, etc. as best determined by the skilled surgeon, thus the illustrations shown are not intended as limitations of patterns or other therapeutic parameters that may effect the desired inflection regions.

Another embodiment of the invention is directed to a corneal topography measuring apparatus having an enlarged field of view for obtaining topology data over a selected corneal/scleral region of a cornea. Many devices known to those skilled in the art as topographers, keratometers, corneascopes, and others are available for measuring corneal topology parameters such as shape, radius, surface elevation, and so on. Devices of these types typically operate either on the Placido disk principle, rasterstereography (PAR topography device), or alternatively use a rotating slit, or a scanning slit as in the Orbscan II (Bausch & Lomb Incorporated) anterior segment measuring device. With certain topography measuring apparatus, however, the available instrument field of view may limit the ability to measure corneal/scleral parameters over the desired measurement region. The cornea is approximately 11.75 mm wide and about 10.6 mm high (*Wolff's Anatomy of the Eye and Orbit*, 8$^{th}$ edition, page 217). However, the inventor is not aware of a diagnostic topography device having a 10 mm×10 mm or greater (H×V) field of view. Due to the recognized difficulties of capturing a live eye, the field of view should advantageously be somewhat larger than the necessary minimum size to allow for some amount of tolerance in the position of the eye during acquisition. According to the instant embodiment, a topography device provides a field of view in the vertical direction of at least 10 mm and in the horizontal direction of at least 10 mm. More particularly, a 10 mm×14 mm field of view is suggested. In an exemplary aspect, the field of view of the device is 13.25 mm (V)×16.5 mm (H).

A measurement technique based on the principal known as rasterstereography is advantageously useful for corneal/scleral measurements because the field of view provided by this type of apparatus can be sufficiently extended beyond the limbus and into the scleral region. A commercial rasterstereography apparatus and methodology are described in U.S. Pat. Nos. 4,995,716 and 5,159,361, both of which disclosures are hereby incorporated by reference in their entirety to the fullest allowable extent. Various modification of the current commercially available system affecting measurement accuracy, field of view, spatial sampling (grid design) and depth of field will advantageously provide expanded measurement capabilities.

An rasterstereographic corneal topography ("RCT") system according to an exemplary embodiment of the invention will have the following parameters:

The camera uses a sensor (e.g., CCD or others known in the art) with dimensions:
  Width (W): 6.6 mm;
  Height (H): 5.3 mm;

The captured image will have dimensions:
  Width: 1280 Pels (picture elements)
  Height: 1024 Pels Field of view (approximated):
  Width: 16.5 mm
  Height=13.25 mm.

Grid camera magnification (approximated):
  M=−0.4

Current grid imaging lens focal length:
  f: 75 mm.

Source of projection grid illumination:
  λ: High intensity LED

Pixel resolution at the object plane (approximated):

Res: 0.013 mm/Pel

Grid Design

Figure 8:
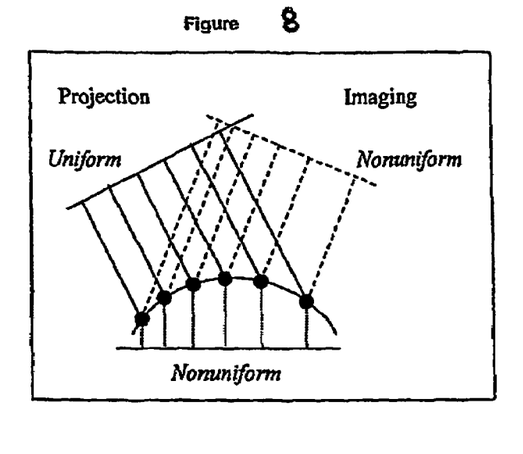
FIGS. 8, 9 and 10 are line drawings illustrating various projection and imaging beam arrangements for a grid of a rasterstereographic topography system according to an embodiment of the invention.
Figure 9:
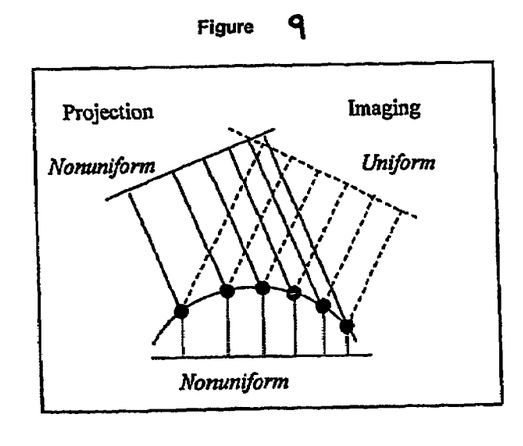
Figure 10:
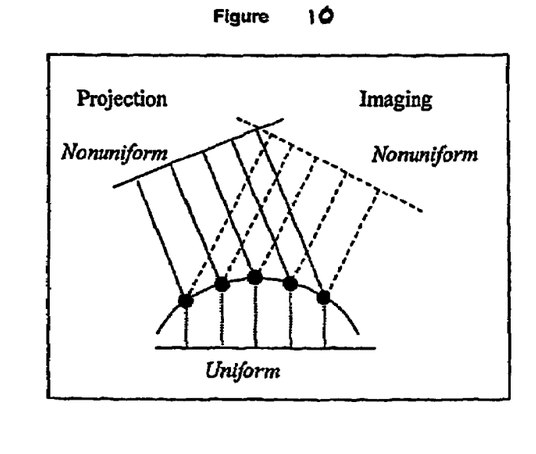

Accuracy of the measurements depends on, among other things, the spatial sampling of the surface (e.g. cornea) under test. Three aspects of grid patterns are illustrated in FIGS. 8, 9, and 10. In FIG. 8, the projection arm has equally spaced grids. In this case, the spatial samples on a convex surface are nonuniformly spaced as are the grid intersections captured by the imaging arm. In order to increase the spatial sampling by decreasing the spacing in the uniform projected grid, care must be taken that the grid captured in the imaging arm is not too tightly packed to be resolved by image processing.

Conceptually, it is a simple matter to modify (pre-warp) the grid spacing in the projection arm so that the grid intersections captured by the imaging arm are uniformly spaced. This is illustrated in FIG. 9. The uniformly spaced grid in the captured image will permit higher spatial resolution while reducing the chance for image processing difficulties noted for the system aspect in FIG. 8.

In an alternative aspect, the projection grid can be pre-warped such that the grid spacing is uniform on a given prototype surface as illustrated in FIG. 10. The distortion of the grid captured by the imaging arm will be similar to that in the projection arm. This magnitude of the distortion of the grid in the projection and imaging arms of the system in FIG. 10 will be less than that when either a uniform grid in the projection (FIG. 8) or imaging (FIG. 9) arms is employed. This aspect of the grid pattern maximizes the spatial resolution of the corneal/scleral measurement system.

Depth of Field (DOF)

The depth of field is a measure of the tolerance around the object plane that leads to focused objects in the image plane. This is primarily a geometric calculation, but diffraction must also be considered. In the exemplary embodiment of the corneal/scleral measurement system, the depth of field is significantly increased by using "offset" (as opposed to tilted) Scheimpflug projection and imaging arms.

Relationship of Projection Angle to Measurement Accuracy

Figure 11:
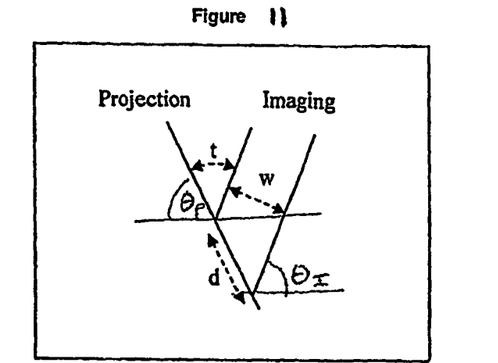
FIG. 11 is a line drawing showing relational parameters between a projection beam and an imaging beam of a rasterstereographic topography system according to an embodiment of the invention.

In order to determine the basic relationship between projection angle and surface measurement accuracy, the projection angle, $\theta_P$, is set to equal the imaging angle, $\theta_I$ due to the symmetry in measuring both left and right eyes. The measurement error employed will be the Euclidean distance between the true surface point and the measured surface point. This includes both height and surface point locations errors as shown in FIG. 11. FIG. 11 shows a projected ray and two imaging rays separated by a distance w. The distance w represents combined image processing and calibration errors referred to the image plane. The surface error distance d is $$d(w,t) = w/\sin[t\pi/180].$$

Figure 12A:
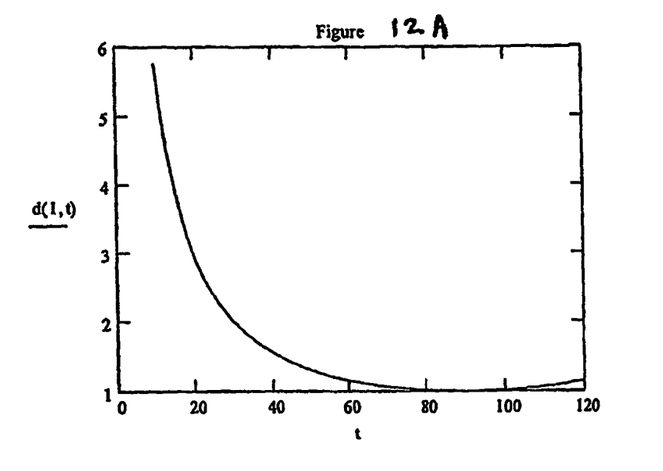
FIGS. 12A and 12B are graphs showing the effect of changing the projection/imaging angle for a fixed position error, w, in a rasterstereographic topography system according to an embodiment of the invention.
Figure 12B:
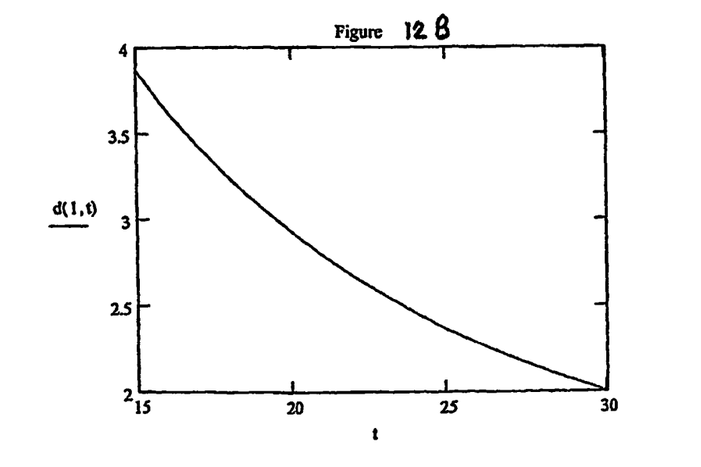

For a fixed position error w, the effect of changing the projection/imaging angle t, is shown in FIG. 12A. An enhanced view of this graph in the region of t=15 to 30 degrees is shown in FIG. 12B. From these graphs, it can be seen that to minimize error, the projection and imaging rays should be orthogonal. However, due to the structure of a subject's face, it is not practical to have the angle increased to 90 degrees. The current exemplary rasterstereography system has this angle at about 24 degrees. At this angle, it may be necessary to turn the patient's head to get an exam that is not occluded by the subject's nose. If this angle is reduced by 5 degrees, so that the head is less likely to be required to be adjusted, the sensitivity for measurement error for a given image processing error is increased by about 25%. Thus, it may be advantageous that the current exemplary projection/imaging angle remain unchanged The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

We claim:

1. A method for enhancing ocular accommodation, comprising:

making a pre-determined biomechanical alteration of a subject's corneal structure outside of an optical zone of the cornea; and using the biomechanical alteration to create an inflection region in the corneal structure, resulting in enhanced corneal accommodative power.

2. The method of claim 1, comprising making a topologic measurement of a corneal/scleral region of the subject's cornea in an accommodative state;

making another topologic measurement of the corneal/scleral region of the subject's cornea in a non-accommodative state; and determining a difference value between one and another topologic measurements.

3. The method of claim 1, wherein making a pre-determined biomechanical alteration of a subject's corneal structure comprises an intrastromal corneal ablation.

* * * * *